(12) United States Patent
Berti-Mattera et al.

(10) Patent No.: US 7,964,585 B2
(45) Date of Patent: Jun. 21, 2011

(54) COMPOSITION AND METHOD OF TREATING PERIPHERAL NEUROPATHY

(75) Inventors: Liliana Berti-Mattera, University Heights, OH (US); Timothy S. Kern, Solon, OH (US)

(73) Assignee: Case Western Reserve University, Cleveland, OH (US)

( * ) Notice: Subject to any disclaimer, the term of this patent is extended or adjusted under 35 U.S.C. 154(b) by 1007 days.

(21) Appl. No.: 11/685,377

(22) Filed: Mar. 13, 2007

(65) Prior Publication Data

US 2007/0244077 A1 Oct. 18, 2007

Related U.S. Application Data (60) Provisional application No. 60/782,031, filed on Mar. 14, 2006.

(51) Int. Cl.
*A61K 31/609* (2006.01)
*A61K 31/63* (2006.01)

(52) U.S. Cl. ........................................ 514/155; 514/166

(58) Field of Classification Search .................. 514/155, 514/166
See application file for complete search history.

(56) References Cited

U.S. PATENT DOCUMENTS

| 5,007,433 | A | * | 4/1991 | Hermsdorffer et al. ....... 600/555 |
| 5,405,842 | A | | 4/1995 | Silverman |
| 5,985,933 | A | | 11/1999 | Zeitlin |
| 6,271,196 | B1 | | 8/2001 | O'Brien |
| 2003/0199424 | A1 | | 10/2003 | Smith et al. |
| 2005/0271661 | A1 | | 12/2005 | Manivasakam et al. |

FOREIGN PATENT DOCUMENTS

WO WO-03032969 A2 4/2003
* cited by examiner

*Primary Examiner* — Jennifer M Kim
(74) *Attorney, Agent, or Firm* — Tarolli, Sundheim, Covell & Tummino LLP (57) ABSTRACT

A method of treating diabetic neuropathy in a subject includes administering to a subject having diabetes or at risk of diabetes a therapeutically effective amount of a pharmaceutical composition comprising at least one of sulfasalazine or a composition including 5-aminosalicyclic acid and sulfapyridine.

12 Claims, 4 Drawing Sheets

COMPOSITION AND METHOD OF TREATING PERIPHERAL NEUROPATHY

RELATED APPLICATION

The present application claims priority from U.S. Provisional Application No. 60/782,031, filed Mar. 14, 2006, which is herein incorporated by reference in its entirety.

GOVERNMENT FUNDING

This invention was made with government support under Grant No. NIH-EY00300 awarded by the National Institutes of Health. The government has certain rights in the invention.

FIELD OF THE INVENTION

The present invent relates to compositions and methods for preventing, inhibiting, and/or treating peripheral neuropathy and, particularly relates, to compositions and methods for preventing, inhibiting, and/or treating abnormal pain perception associated with diabetic neuropathy.

BACKGROUND

Peripheral neuropathy is one of the major complications of diabetes mellitus. Both a decrease in nerve conduction velocity and increased resistance to conduction failure caused by ischemia are among the earliest changes detected in diabetic patients and animal models of the disease. Ultrastructural studies have demonstrated changes in both axons and Schwann Cells (SC) (e.g., decrease in axon caliber and segmental demyelination) as well as in the microvasculature, all of which appear to develop independently. Some studies concluded that the progressive loss of fibers in peripheral nerves observed in human diabetic neuropathy may be due, at least in part, to delayed nerve degeneration and impaired nerve regeneration. Metabolic and microvascular abnormalities, as well as a deficiency in neurotrophins, have been considered responsible for the pathogenesis of diabetic neuropathy. The vascular alterations in diabetes consists mainly of ischemia and endoneurial hypoxia. The mechanisms underlying these vascular abnormalities include degenerative changes in the sympathetic nerve endings of vasa nervorum, with the consequent impairment in neural control of nerve blood flow and reduced production of prostacyclin and nitric oxide in nerves. Since most of these alterations are ameliorated by antioxidant therapies, it has been hypothesized that oxidative stress plays a central role in the pathogenesis of diabetic complications.

Two distinct clinical manifestations of diabetic neuropathy are those represented by patients suffering from painful symmetrical polyneuropathy, and by patients with insensitive, painless feet. There is still controversy regarding the nature of these two syndromes. The painless neuropathy is the prevalent disorder and, according to several studies, is likely to reflect the degree of nerve degeneration. The painful syndrome, on the other hand, is associated with fewer morphological abnormalities. While it has also been proposed that the painful syndrome may reflect nerve regeneration, as opposed to degeneration, several reports suggest that nerve regeneration is impaired in diabetes. Analysis of several functional indices in peripheral sensory nerves of diabetic rodents also suggests depressed, rather than increased, function. For instance, experimental diabetes induces several nociceptive responses including early thermal hyperalgesia that with time turns into hypoalgesia, mechanical hyperalgesia, thermal and tactile allodynia, increased C fiber activity and reduced sensitivity to opioids. In this context, mechanical hyperalgesia may result from increased firing after sustained suprathreshold mechanical stimulation of C fibers.

While therapies with antioxidants, vasodilators and neurotrophins may reverse some functional and metabolic abnormalities in diabetic nerves, they only result in a partial amelioration of abnormal pain perception, suggesting that other pathways are at play.

SUMMARY OF THE INVENTION

The present invention is based on the discovery that sulfasalazine is effective in the treatment and/or prevention of abnormal pain perception (e.g., tactile allodynia and thermal hypoalgesia) associated with diabetic neuropathy. In one aspect, therefore, the invention provides methods for the treatment (or prevention) of diabetic neuropathy in a subject having diabetes or at risk of diabetes. The neuropathic condition is treated by administering to the subject a therapeutically effective amount of a pharmaceutical composition comprising a sulfasalazine and/or its metabolites, 5-aminosalicyclic acid and sulfapyridine. The pharmaceutical composition can also include a pharmaceutically acceptable carrier and/or diluent. The pharmaceutical composition may be administered by injection, by topical application or by the oral route including sustained-release modes of administration, over a period of time and in amounts, which are effective to prevent and/or treat the abnormal pain perception associated with diabetic neuropathy. In an aspect of the invention, the amount of the pharmaceutical composition administered to the subject can be that amount effective to inhibit NFkB expression in nerves involved in nociception in the diabetic subject.

In another aspect, the present invention relates to a pharmaceutical composition for the treatment of diabetic neuropathy in a subject having diabetes or at risk of diabetes. The pharmaceutical composition includes a therapeutically effective amount of a composition comprising a sulfasalazine and/or its metabolites, 5-aminosalicyclic acid and sulfapyridine. The pharmaceutical composition can also include a pharmaceutically acceptable carrier and/or diluent. The pharmaceutical composition may be administered by injection, by topical application or by the oral route including sustained-release modes of administration, over a period of time and in amounts, which are effective to prevent and/or treat the abnormal pain perception associated with diabetic neuropathy. In an aspect of the invention, the amount of the pharmaceutical composition administered to the subject can be that amount effective to inhibit NFkB expression in nerves involved in nociception in the diabetic subject.

The present invention further relates to a method of treating peripheral neuropathy associated with an increase in NFkB expression in nerves involved in nociception in the subject. In the method, a pharmaceutical composition comprising a sulfasalazine and/or its metabolites, 5-aminosalicylic acid and sulfapyridine is administered to the subject. The pharmaceutical composition can also include a pharmaceutically acceptable carrier and/or diluent. The pharmaceutical composition may be administered by injection, by topical application or by the oral route including sustained-release modes of administration, over a period of time and in amounts that are effective to prevent and/or treat the peripheral neuropathy. In an aspect of the invention, the amount of the pharmaceutical composition administered to the subject can be that amount effective to inhibit NFkB expression in nerves involved in nociception in the subject.

The present invention further relates to a method of inhibiting NFkB expression and increasing p-CREB level in nerves involved in nociception in a subject with a peripheral neuropathy. In the method, a pharmaceutical composition comprising a sulfasalazine and/or its metabolites, 5-aminosalicylic acid and sulfapyridine is administered to the subject. The pharmaceutical composition can also include a pharmaceutically acceptable carrier and/or diluent. The pharmaceutical composition may be administered by injection, by topical application or by the oral route including sustained-release modes of administration, over a period of time and in amounts that are effective to prevent and/or treat the peripheral neuropathy. In an aspect of the invention, the amount of the pharmaceutical composition administered to the subject can be that amount effective to inhibit NFkB expression and increase the p-CREB levels in the nociceptive nerves of the subject.

DETAILED DESCRIPTION

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 20% or 10% to a reference quantity, level, value, dimension, size, or amount.

The term "allodynia" as used herein refers to the pain that results from a non-noxious stimulus, i.e., pain due to a stimulus that does not normally provoke pain. Examples of allodynia include, but are not limited to, thermal allodynia, tactile allodynia (pain due to light pressure or touch), and the like.

The term "causalgia" as used herein refers to the burning pain, allodynia, and hyperpathia after a traumatic nerve lesion, often combined with vasomotor and sudomotor dysfunction and later tropic changes.

By "complex regional pain syndromes" is meant the pain that includes, but is not limited to, reflex sympathetic dystrophy, causalgia, sympathetically maintained pain, and the like.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "effective amount", in the context of treating or preventing a condition is meant the administration of that amount of active to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

By "hyperalgesia" is meant an increased response to a stimulus that is normally painful.

By "hypoalgesia" is meant a decreased response to a stimulus that is normally painful.

By "neuropathic pain" is meant any pain syndrome initiated or caused by a primary lesion or dysfunction in the peripheral or central nervous system. Examples of neuropathic pain include, but are not limited to, thermal or mechanical hyperalgesia, thermal or mechanical allodynia, diabetic pain, entrapment pain, and the like.

"Nociceptive pain" refers to the normal, acute pain sensation evoked by activation of nociceptors located in non-damaged skin, viscera and other organs in the absence of sensitization.

The term "pain" as used herein is given its broadest sense and includes n unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28$^{th}$ Edition, W. B. Saunders Company, Philadelphia, Pa.). The goal of treatment of pain is to reduce the degree of severity of pain perceived by a treatment subject.

By "pharmaceutically acceptable carrier" is meant a solid or liquid filter, diluent or encapsulating substance that may be safely used in topical, local or systemic administration.

The term "pharmaceutically compatible salt" as used herein refers to a salt which is toxicologically safe for human and animal administration. This salt may be selected from a group including hydrochlorides, hydrobromides, hydroiodides, sulphates, bisulphates, nitrates, citrates, tartrates, bitartrates, phosphates, malates, maleates, napsylates, fumarates, succinates, acetates, terephthalates, pamoates and pectinates.

The terms "subject" or "individual" or "patient", used interchangeably herein, refer to any subject, particularly a vertebrate subject, and even more particularly a mammalian subject, or whom therapy or prophylaxis is desired. Vertebrate animals that fall within the scope of the invention include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). An example of a subject is a human in need of treatment or prophylaxis for a peripheral neuropathic condition, especially diabetic neuropathy or related condition. However, it will be understood that the aforementioned terms do not imply that symptoms are present.

The present invention arises from the discovery that sulfsalazine (SFZ) (5([p(2-pyridylsulfamoyl) phenyl]azo)salicylic acid) and/or its metabolites, 5-aminosalicylic acid and sulfapyridine, are effective in inhibiting NFkB expression and increasing pCREB level in the nerves involved in nociception (i.e., nerves that are involved in the nociception process that contributes to the perception of pain) of a subject with a peripheral neuropathy (e.g., tactile allodynia and thermal hypoalgesia). Additionally, sulfasalazine and/or its metabolites, 5-aminosalicylic acid and sulfapyridine, when administered to diabetic mammals with diabetic neuropathy substantially inhibited NFkB expression, increased pCREB leves, and decreased NO levels in the sciatic nerves of the mammals. These discoveries are based on pre-clinical data that show that sulfasalazine administration to STZ-diabetic rats prevents the onset and development of tactile allodynia and thermal hypoalgesia, the defining symptom of diabetic neuropathy. Remarkably, such desirable outcomes occurred through a mechanism at least partially independent of pathways associated with oxidative stress, which are typically affected by salicylates.

Accordingly, the present invention provides methods for treating and/or preventing abnormal pain perception, such as tactile allodynia and thermal hypoalgesia, associated with diabetic neuropathy. In the method, a therapeutically effective amount of a pharmaceutical composition comprising sulfasalazine or its metabolites, 5-aminosalicyclic acid and sulfapyridine, is administered to a subject at risk of developing or afflicted with diabetic neuropathy.

The subject can be an individual who has been diagnosed with a diabetes, who is suspected of having a neuropathic condition associated with diabetes, who is known to be susceptible and who is considered likely to develop a neuropathic condition associated with diabetes, or who is considered likely to develop a recurrence of a previously treated neuropathic condition associated with diabetes.

In an aspect of the invention, the pharmaceutical composition comprising sulfasalazine and/or its metabolites can act to prevent or attenuate one or more symptoms associated with diabetic neuropathy, such as abnormal pain perception (e.g., tactile allodynia, hyperalgesia, thermal hypoalgesia). The pain associated with the allodynia and/or hyperalgesia may be severe and disabling. The pain can be caused by increased expression, activity, and localization of NFkB in nerves involved in nociception in the diabetic subject. Accordingly, in a related aspect, the invention provides methods for preventing and/or treating peripheral neuropathy, especially peripheral neuropathic pain, associated with increased NFkB expression in a subject. The method can comprise administering to the subject of a pharmaceutical composition that includes a therapeutically effective amount of sulfasalazine or its metabolites, 5-aminosalicylic acid and sulfapyridine.

The peripheral neuropathy can be, for example, a result of diseases of the nerves (primary neuropathy) and neuropathy that is caused by systemic disease (secondary neuropathy), such as but not limited to diabetic neuropathy. Herpes Zoster (shingles)-related neuropathy, uraemia-associated neuropathy, amyloidosis neuropathy, HIV sensory neuropathies, hereditary motor and sensory neuropathies (HMSN), hereditary sensory neuropathies (HSNs), hereditary sensory and autonomic neuropathies, hereditary neuropathies with ulcero-mutilation, nitrofurantoin neuropathy, tumaculous neuropathy, neuropathy caused by nutritional deficiency and neuropathy caused by kidney failure. Other causes include repetitive activities such as typing or working on an assembly line, medications known to cause peripheral neuropathy, such as several AIDS drugs (DDC and DDI), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated infectious processes (such as Guillian-Barre syndrome). In one aspect of the invention, the peripheral neuropathy is an abnormal pain perception diabetic neuropathy or related condition.

In another aspect of the invention, a therapeutically effective amount of pharmaceutical composition for the treatment of peripheral neuropathy is one that is effective for the prevention of a neuropathic condition (e.g., tactile allodynia), including the prevention of incurring a symptom, holding in check such symptoms (e.g., pain), and/or treating existing symptoms associated with the neuropathic condition. When administered to a subject for the treatment of pain associated with diabetic neuropathy and peripheral neuropathy, and effective amount (i) preventing pain experienced by a subject which may be predisposed to the condition but has not yet been diagnosed with the condition and, accordingly, the treatment constitutes prophylactic treatment for the pathologic condition; (ii) inhibiting pain initiation or a painful condition, i.e., arresting its development; (iii) relieving pain, i.e., causing regression of pain initiation or a painful condition; or (iv) relieving symptoms resulting from a disease or condition believed to cause pain, e.g., relieving the sensation of pain without addressing the underlying disease or condition. The therapeutically effective amount can be that amount effective to inhibit NFkB expression, activity/or localization in nerves of the subject.

The present invention also relates to a method of inhibiting NFkB expression and increasing and p-CREB level in nerves involved in nociception of a subject with a peripheral neuropathy. In the method, a pharmaceutical composition comprising a sulfasalazine and/or its metabolites, 5-aminosalicylic acid and sulfapyridine is administered to the subject. In an aspect of the invention, the amount of the pharmaceutical composition administered to the subject can be that amount effective to inhibit NFkB expression and increase the p-CREB levels in nerves of the subject.

The pharmaceutical composition used in the methods can include any known sulfasalazine composition and/or composition comprising its metabolites, 5-aminosalicylic acid and sulfapyridine, provided that the sulfasalazine and/or its metabolites are pharmaceutically active. A "pharmaceutically active" sulfasalazine and/or a compound comprising 5-aminosalicylic acid and sulfapyridine is in a form which results in the prevention and/or treatment of a neuropathic condition (e.g., tactile allodynia), including the prevention of incurring a symptom, holding in check such symptoms, and/or treating existing symptoms associated with the neuropathic condition, when administered to an individual.

The effect of pharmaceutical compositions of the present invention may be examined by using one or more of the published models of pain/nociception or of neuropathy, especially peripheral neuropathy, and more especially painful diabetic neuropathy, known in the art. This may be demonstrated, for example using a model, which assesses the onset and development of tactile allodynia, the defining symptom of painful diabetic neuropathy, as for example described herein. The effects and/or activity of the sulfasalazine and/or a compound comprising 5-aminosalicylic acid and sulfapyridine can be evaluated by any method known in the art. Examples of such methods are the Tail-flick test (D'Amour et al. 1941, J. Pharmacol. Exp. and Ther. 72: 74-79); the Rat Tail Immersion Model, the Carrageenan-induced Paw Hyperalgesia Model, the Formalin Behavioral Response Model (Dubuisson et al, 1977, Pain 4: 161-174), the Von Frey Filament Test (Kim et al., 1992, Pain 50: 355-363), the Radiant Heat Model, the Cold Allodynia Model (Gogas et al., 1997, Analgesia 3: 111-118), the paw pressure test Randall and Selitto, 1957, Arch Int Pharmacodyn 111: 409-419) and the paw thermal test (Hargreaves et al., 1998, Pain 32: 77-88). Pharmaceutical compositions which test positive in such assays can be for the prevention of neuropathic pain found, for example, in diabetic patients.

The active compounds of the present invention, i.e., sulfasalazine and/or its metabolites may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Pharmaceutical compositions that can be used in the present invention include compositions wherein the pharmaceutically active compounds are contained in an effective amount to achieve their intended purpose. The dose of active compounds administered to a patient should be sufficient to achieve a beneficial response in the patient over time such as a prevention or reduction in at least one symptom associated with a neuropathic condition, which is suitably neuropathic pain such as diabetic neuropathic pain. The quantity of the pharmaceutically active compounds(s) to be administered may depend on the subject to be treated inclusive of the age, sex, weight and general health condition thereof. In this regard, precise amounts of the active compound(s) for administration will depend on the judgement of the practitioner. In determining the effective amount of the active compound(s) to be administered in the prophylaxis of the neuropathic condition, the physician may evaluate numbness, weakness, pain, and loss of reflexes. In any event, those of skill in the art may readily determine suitable dosages sulfasalazine and/or a compound comprising 5-aminosalicylic acid and sulfapyridine.

In one aspect, and dependent on the intended mode of administration, the compositions containing sulfasalazine and/or its metabolites will generally contain about 0.1% to 90%, about 0.5% to 50%, or about 1% to about 25%, by weight of sulfasalazine and/or its metabolites, the remainder being, for example, pharmaceutical carriers and/or diluents. Usually, a daily dose of the sulfasalazine and/or a compound comprising a sulfapyridine moiety, may be from about 10 mg/kg BW to about 300 mg/kg of BW per day, from about 100 mg to 200 mg/kg BW or about 200 mg/kg BW. The dosage of the sulfasalazine and/or its metabolites can depend on a variety of factors, such as mode of administration, the species of the affected subject, age and/or individual condition.

The active compounds may be formulated and administered systemically, topically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the therapeutic agents of the invention may be formulated in aqueous solutions, suitably in physiologically compatible buffers such as Hanks' solution, Rinter's solution, or physiological saline buffer. For transmucosal administration, penetrants appropriate to the barrier to be permeated are used in the formulation. Such penetrants are generally known in the art.

Alternatively, the compositions of the invention can be formulated for local or topical administration. In this instance, the subject compositions may be formulated in any suitable manner, including, but not limited to, creams, gels, oils, ointments, solutions and suppositories. Such topical compositions may include a penetration enhancer such as benzalkonium chloride, digitonin, dihydrocytochalasin B, capric acid, increasing pH from 7.0 to 8.0. Penetration enhancers which are directed to enhancing penetration of the active compounds through the epidermis are preferred in this regard. Alternatively, the topical compositions may include liposomes in which the active compounds of the invention are encapsulated.

The compositions of this invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as nonionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the active compounds of the present invention can be formulated readily using pharmaceutically acceptable carriers well known in the art into dosages suitable for oral administration, which is also preferred for the practice of the present invention. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatin, talc, calcium sulphate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose-, sodium caroxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilising processes.

Dragee cores can be provided with coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceuticals which may be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stailizers. In soft capsules, the active compounds may be dissolved or suspended in suitable liquids, such as fatty oils, liquid paraffin, or liquid polyethylene glycols. In addition, stabilizers may be added.

Dosage forms of the active compounds of the invention may also include injecting or implanting controlled releasing devices designed specifically for this purpose or other forms of implants modified to act additionally in this fashion. Controlled release of an active compound of the invention may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be achieved by using other polymer matrices, liposomes and/or microspheres.

The sulfasalazine and/or a compound comprising 5-aminosalicylic acid and sulfapyridine may be administered over a period of hours, days, weeks, or months, depending on several factors, including the severity of the neuropathic condition being treated, whether a recurrence of the condition is considered likely, etc. The administration may be constant, e.g., constant infusion over a period of hours, days, weeks, months, etc. Alternatively, the administration may be intermittent, e.g., active compounds may be administered once a day over a period of days, once an hour over a period of hours, or any other such schedule as deemed suitable.

The compositions of the present invention may also be administered to the respiratory tract as a nasal or pulmonary inhalation aerosol or solution for a nebuliser, or as a microfine powder for insufflation, alone or in combination with an inert carrier such as lactose, or with other pharmaceutically acceptable excipients. In such a case, the particles of the formulation may advantageously have diameters of less than 50 micrometers, suitably less than 10 micrometers.

In order that the invention may be readily understood and put into practical effect, particular embodiments will now be described by way of the following non-limiting examples.

Example

We obtained promising results by demonstrating the effectiveness of SFZ (sulfasalazine) at improving tactile allodynia in experimentally diabetic rats. SFZ acts not only as an antioxidant and inhibitor of NFkB and cycloxygenases, but also appears to mediate neuroprotection. We observed that a 3 month treatment with SFZ completely prevents the development of tactile allodynia in diabetic rats by a mechanism that is at least partially independent of its anti-oxidant action. This complete prevention contrasts with the effects of other salicylates that only attenuate neuropathic pain.

Based on this information, we believe that the development of tactile allodynia in experimental diabetes reflects alterations in one or more SFZ targets in noiceptive fibers. These alterations can include changes in the expression, activity, and/or localization of the transcription factors NFkB and CREB in the different compartments of sciatic nerves and dorsal root ganglia. Treatment of diabetic rats with SFZ prevents the alteration in expression, activity, and localization of NFkB and cREB, two known mediators of pain. The beneficial effects to SFZ on the development of tactile allodynia extend to other alterations that characterize diabetic neuropathy, such as thermal hypoalgesia and the deficits in nerve conduction velocity and blood flow.

Results

SFZ Treatment Completely Prevents the Development of Tactile Allodynia

Figure 1:
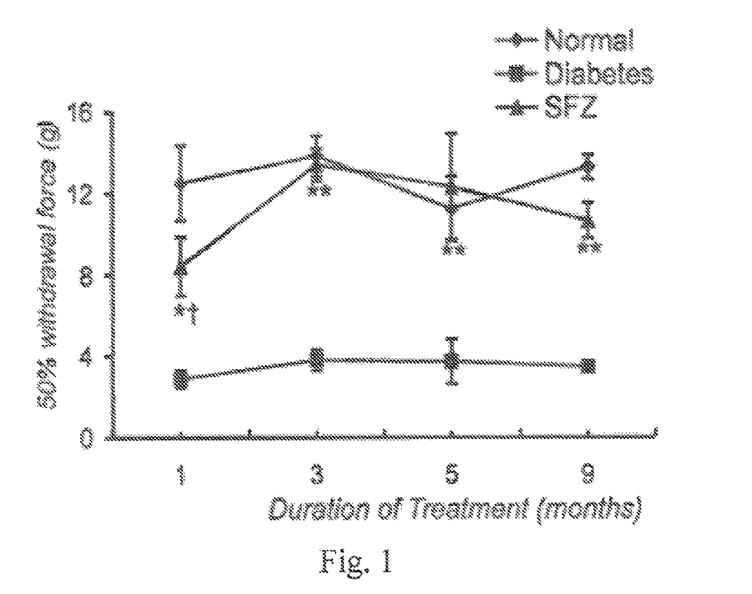
FIG. 1 is a plot illustrating that sulfasalazine prevents the development of tactile allodynia in experimentally diabetic rats. Streptozotocin-induced diabetic rats (6-8 animals per group) were either left untreated or subjected to treatment with SFZ for up to 9 months. The presence of tactile allodynia was investigated at different time-points. Results shown represent the mean±SEM of the averages of the thresholds measured on the left and right paw of each animal. * and **, significantly different from diabetic animals at $P<0.05$ and $P<0.01$; †, significantly different from normal animals at $P<0.05$ as calculated by ANOVA followed by Dunnett's test.
Figure 2:
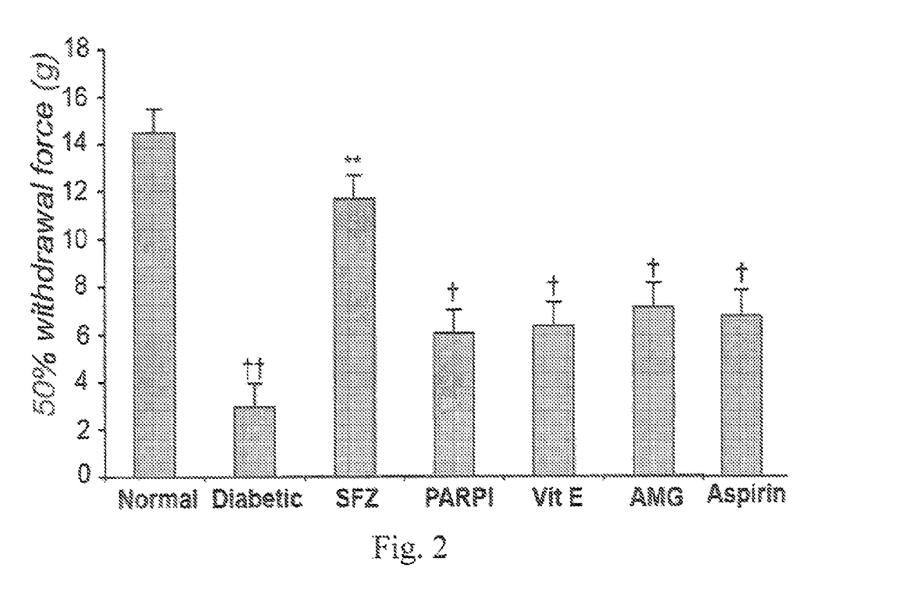
FIG. 2 is a plot illustrating that sulfasalazine is the most effective drug in our panel for the prevention of tactile allodynia in experimentally diabetic rats. Diabetic rats were either left untreated or subjected to treatment with either SFZ, the PARP inhibitor PJ-34, vitamin E (Vit E), or aminoguanidine (AMG) for 3 months. At the end of this period, the presence of tactile allodynia was evaluated by comparison with the responses obtained in normal animals (6-8 animals were present in each experimental group). **, significantly different from diabetic animals at $P<0.01$; † and ††, significantly different from normal animals at $P<0.05$ and $P<0.01$, respectively, as calculated by ANOVA followed by Dunnett's test.

Experimentally diabetic rats display tactile allodynia (i.e., the perception of non-painful stimuli as painful), as evidenced by a significant decrease in the 50% withdrawal force (force at which there is a 50% probability of withdrawal) to von Frey filaments (FIGS. 1 and 2). The tactile allodynia was evident as early as 1 month after induction of diabetes and persisted throughout the experimental period (FIG. 1). Importantly, when compared to the non-treated diabetic group, administration of SFZ (150 mg/kg BW, daily, added to drinking water) prevented the development of tactile allodynia in either 50% or 80-100% of the animals after one or three months of treatment, respectively. We compared the effect of SFZ treatment on tactile allodynia in experimentally diabetic rats with those elicited by other salicylates (i.e. aspirin, 0.3 mg/kg), by the anti-oxidants Vitamin E (VIT E; 4 g/kg diet) and by aminoguanidine (AMG; 3 g/kg diet) and by the poly-ADP ribose-polymerase (PARP) inhibitor PJ-34 (20 mg/kg, daily, added to drinking water). In contrast to SFZ, administration of either aspirin, VIT E, AMG or PJ-34 only resulted in a partial prevention of tactile allodynia in experimentally diabetic rats (FIG. 2).

Experimentally diabetic rats display nociceptive alterations in addition to tactile allodynia. In this context, evaluation of streptozotocin-induced diabetic rats using the Randall and Selitto test showed that these animals also develop mechanical hyperalgesia (evidenced by an approximately 50% decrease in the withdrawal thresholds to painful, high-intensity, linearly-applied increasing stimuli) (results not shown). However, and in contrast to the beneficial effects observed on tactile allodynia in diabetic rats, treatment with SFZ only resulted in a modest amelioration of the mechanical thresholds that was not statistically significant (not shown).

These results demonstrate that SFZ prevents tactile allodynia in an experimental model of diabetes. At the same time, our observations suggest that pathways other than oxidative stress are involved in the development of tactile allodynia, and that these additional pathways are sensitive to treatment with SFZ.

Mice Lacking Expression of p105 NFkB (The Precursor of the p50 Subunit of NFkB) do not Develop Tactile Allodynia Following Induction of Experimental Diabetes To address the role of the NFkB pathway in the development of enhanced nociception in diabetes, we compared the effect of experimental diabetes on pain thresholds to low-intensity stimuli (evaluation of tactile allodynia) in wild type and p105 NFkB knockout mice (B6129PF2/J and NFkBp105 ko, respectively). As expected, 5-month old diabetic B6129PF2/J mice developed tactile allodynia (Table 1). Interestingly, normal and diabetic NFkBp105 ko displayed withdrawal thresholds similar to those of normal B6129PF2/J mice (Table 1). These results suggest that enhanced activation of NFkB may be critical to the development of tactile allodynia in experimental diabetes. This may reflect either a direct role of this transcription factor on the hyperactivity of selective nerve fibers or, alternatively, a secondary effect on other nerve/tissue compartments, such as endothelial cells.

TABLE 1

NFkB knockout diabetic mice do not develop tactile allodynia.

| | Withdrawal Threshold (g) | |
|---|---|---|
| | B6129PF2/J (wild type mouse) | NFkBp105 ko knockout |
| Normal | 4.16 ± 0.90 | 5.80 ± 0.51 |
| Diabetic | 1.67 ± 0.89** | 5.52 ± 0.94 |

Results represent the mean ± SD of four animals.

Figure 3:
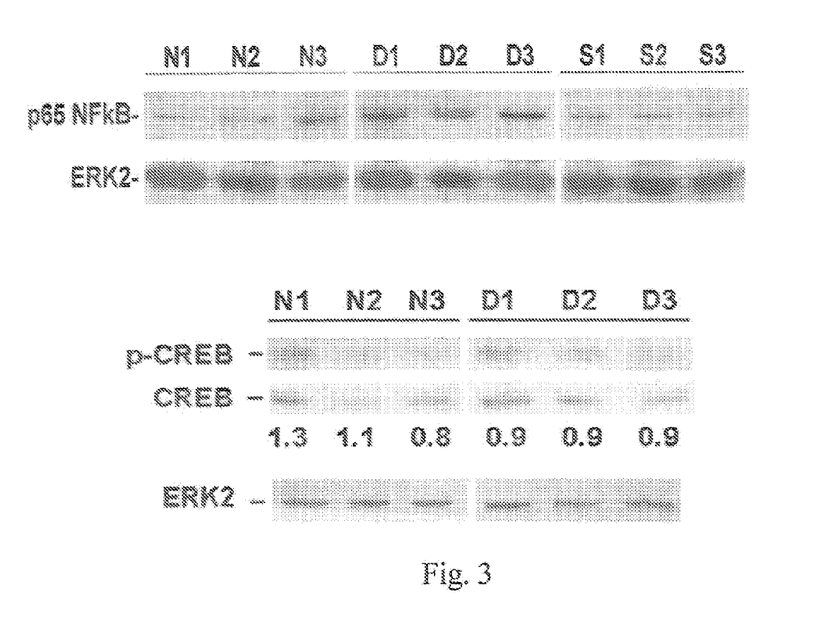
FIG. 3 is a Western blot analysis of p65 NFkB and CREB expression in sciatic nerves from individual normal (N), 3-month diabetic (D) and 3-month SFZ-treated diabetic (S) rats. Nerve proteins were subjected to SDS-PAGE and immunoblotting with antisera against p65 NFkB (left panel) or total (CREB) and phosphorylated CREB (p-CREB) (right panel). The ratio between the levels of pCREB and total CREB, in arbitrary units, is shown at the bottom of the respective lanes (numbers underneath the lanes). Blots were also probed using anti-ERK2 to control for protein loading.

Immunochemical Detection of NFkB, CREB and phospho-CREB in Sciatic Nerve Homogenates from Normal and Diabetic Rats We carried out preliminary studies to determine the ability of commercial antibodies to detect the p65 subunit of NFkB, phospho-CREB (p-CREB) and CREB in sciatic nerve extracts (FIG. 3), as well as the possible changes in the expression of these transcription factors during experimental diabetes. The signal detected in the immunoblots is likely to reflect the presence of these transcription factors in Schwann cells, fibroblasts and/or endothelial cells. Importantly, we observed that, 3 months after the onset of experimental diabetes, there is an increase n the expression of p65 NFkB in sciatic nerves that can be prevented by SFZ treatment (FIG. 3, left panel). We are currently performing electrophoretic mobility shift assays (EMSA) to determine whether the increased immunoreactivity of p65 NFkB in diabetic nerves is paralleled by an increase in NFkB activity. At the same time, we observed a modest decrease in the levels of p-CREB relative to total CREB in diabetic nerves (FIG. 3, right panel). The decrease in p-CREB immunoreactivity, and presumably in the activity of this factor in diabetic nerves, is in agreement with similar studies in normal and diabetic DRG and might reflect alterations in neurotrophic support that characterize this disease. The SFZ-sensitive increased expression of p65 NFkB in diabetic nerves is consistent with the notion that this transcription factor may play an important role in nociceptive alterations triggered by experimental diabetes.

Figure 4:
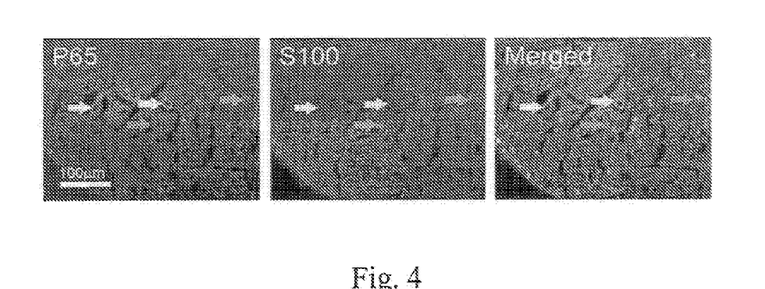
FIG. 4 are photographs illustrating localization of p65 NFkB in sciatic nerves. Tissue sections were fixed and double-labeled with rabbit anti-p65NFkB (Santa Cruz) and mouse anti-S100 (Sigma). Light arrows: blood vessels; Dark arrows: Schwann cells.

Immunohistochemical Detection of p65 NFkB in Cross Sections of Normal Sciatic Nerves Results depicted in FIG. 4 show the expression of p65-NFkB in blood vessels (light arrows) and Schwann cells (co-localization of p65 staining with S100, a marker of Schwann cells (dark arrows).

Figure 5:
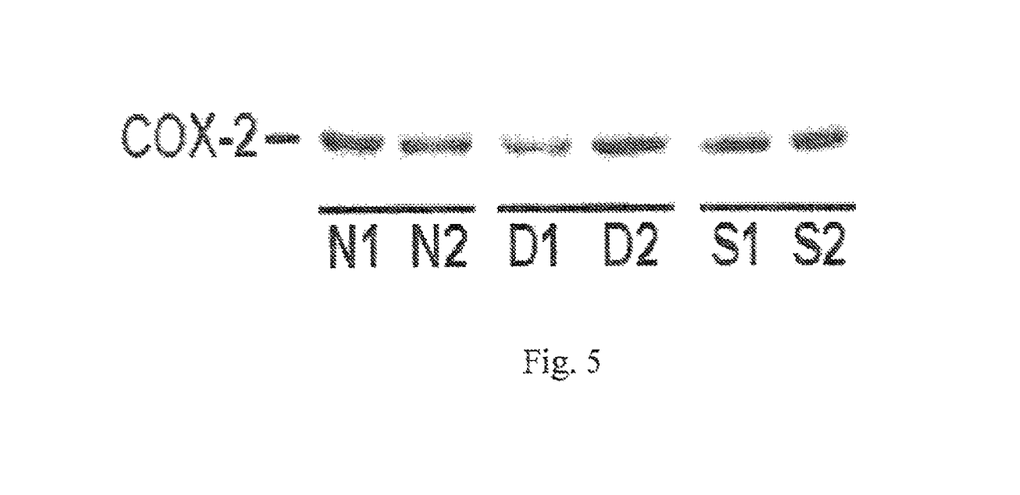
FIG. 5 is a Western blot analysis of COX-2 immunoreactivity in sciatic nerve samples. Epineurim-free sciatic nerve extracts from normal (N), 3-month diabetic (D) and 3-month SFZ-treated diabetic (S) rats were subjected to SDS-PAGE and immunoblotting with anti-COX-2 antiserum (Cayman).

SFZ Modulates Levels of NO and $PGE_2$ in Sciatic Nerves from 9-Month Diabetic Rats NO levels were assayed in extracts from sciatic nerves (epineurium-free) by measuring the stable metabolites of NO (nitrate+nitrite) using a fluorometric assay kit. At the same time, the levels of $PGE_2$ were evaluated by ELISA using a commercial kit (Cayman Chemical). In parallel samples, we also performed an immunoblot analysis to investigate possible changes in the expression of COX-2, one of the enzymes that convert arachidonic acid into $PGE_2$. We observed that although diabetic sciatic nerves do not exhibit changes in NO and $PGE_2$, treatment of diabetic rats with SFZ results in a significant decrease in NO and appears to increase $PGE_2$ levels (in these preliminary experiments, the effect on $PGE_2$ was not statistically significant) (Table 2). On the other hand, we did not observe any significant changes in the expression of COX-2 (FIG. 4), when comparing the normal, diabetic and SFZ-treated diabetic animals (FIG. 5). Previous observations suggested a role for increased NO production in the development of hyperalgesia and allodynia, and also a neuroprotective role for $PGE_2$ following nerve injury. While our observations are not fully consistent with a role of NO in tactile allodynia during experimental diabetes (comparison of normal and diabetic animals in Table 2), it is nonetheless possible that SFZ may also prevent the development of tactile allodynia by additional effects on NO- and/or $PGE_2$-dependent pathways.

TABLE 2

Treatment of experimentally diabetic rats with SFZ

|  | NO (nmoles/mg protein) | $PGE_2$ (pmoles/mg protein) |
|---|---|---|
| Normal | 5.04 ± 0.06 | 143 ± 11 |
| Diabetic | 5.52 ± 0.30 | 149 ± 48 |
| SFZ-treated | 3.08 ± 0.25** | 366 ± 220 |

Treatment of experimentally diabetic rats with SFZ (200 mg/Kg BW, daily for 9 months) affects levels of NO and $PGE_2$ in sciatic nerves. Results represent the mean ± SD of 3 animals.
**Significantly different from diabetic or normal animals at P < 0.01, as calculated by one-way ANOVA followed by Dunnett's test.

Effect of SFZ on Levels of Adenosine Derivatives in Diabetic Sciatic Nerves

Figure 6:
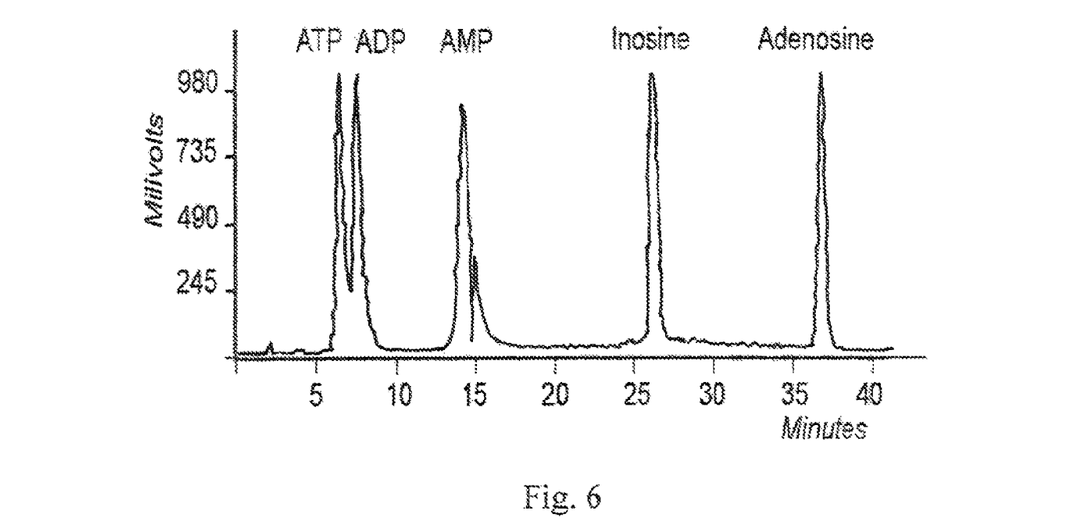
FIG. 6 is a plot illustrating HPLC separation of adenine nucleotides and inosine standards.
Figure 7:
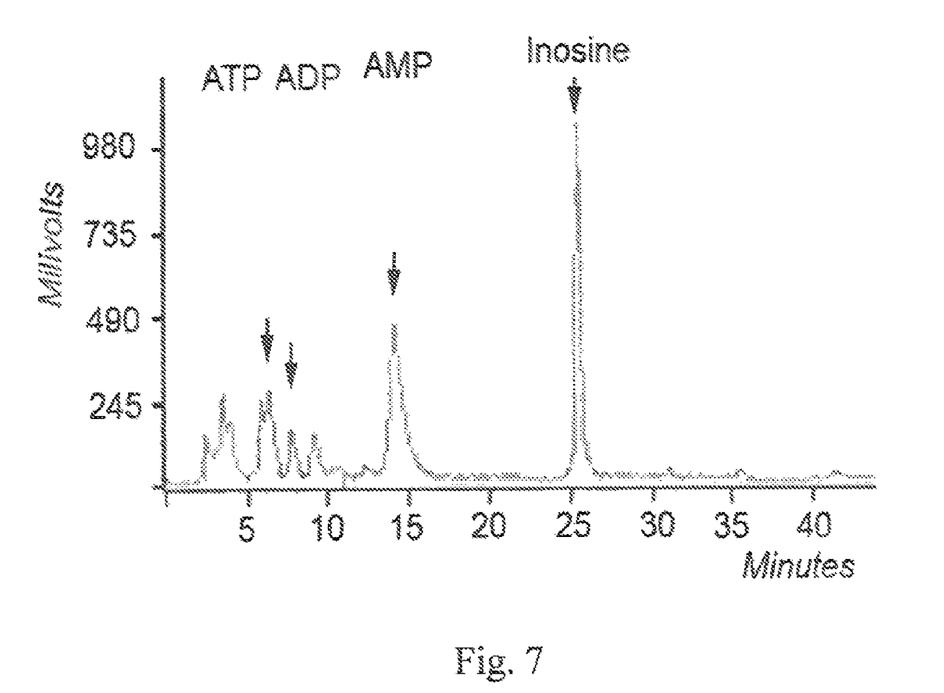
FIG. 7 is a plot illustrating HPLC separation of diabetic sciatic nerve homogenates.

Administration of either adenosine or of adenosine kinase or adenosine deaminase inhibitors appears to increase nociception thresholds. Two studies have reported that acute administration of either adenosine or adenosine kinase inhibitors can prevent some nerve abnormalities in experimental diabetes. These studies suggest that a deficit in the levels of adenosine may be responsible for abnormal pain perception in experimental diabetes. However, no studies have investigated the eventual changes in levels of adenosine (or its metabolites) in diabetic nerves. Interestingly, it has been reported that SFZ can increase extracellular levels of adenosine. Given these precedents, and to determine whether the beneficial effects of SFZ might be mediated through changes in adenosine levels, we measured the levels of this nucleoside in sciatic nerve extracts. Separation of adenosine derivatives was performed by reverse-phase HPLC in 18:8 columns. This method allows proper separation of ATP, ADP, AMP, adenosine and inosine standards (FIG. 6). An example of an elution profile corresponding to HPLC separation of a diabetic nerve homogenate is shown in FIG. 7. Under our experimental conditions we didn't detect an adenosine peak in the sciatic nerve extracts, but we typically observed small peaks corresponding to ATP and ADP and two relatively large peaks corresponding to AMP and inosine (a metabolite obtained by deamination of adenosine) (FIG. 7). The lack of an adenosine peak following fractionation of the sciatic nerve extracts is consistent with metabolism to AMP and/or with the presence of significant adenosine deaminase activity in these samples (and complete degradation to inosine and other breakdown products). In this context, and given the recent demonstration that inosine is a potent agonist for the $A_1$ and $A_3$ receptors, it is possible to hypothesize that this nucleoside might represent the predominant agonist for adenosine receptors in sciatic nerves.

The analysis of the elution profiles corresponding to sciatic nerve extracts prepared from normal, diabetic and SFZ-treated diabetic rats is summarized in Table 3. We observed that the SFZ-treated diabetic rats display an increase of inosine and a decrease in AMP levels. The design of these experiments could be improved to include the derivatization of samples (and increase the resolution of the ATP and ADP peaks) and/or dual analysis of samples to improve separation of overlapping components. However, the absence of a trend showing changes in diabetic samples and their reversal following SFZ treatment suggests, in principle, that the changes in the levels of adenosine metabolites may not play a major role in this pathology.

TABLE 3

Treatment of diabetic rats with SFZ

|  | Inosine (nmoles/mg protein) | AMP (nmoles/mg protein) | Inosine/AMP |
|---|---|---|---|
| Normal | 3.92 ± 0.47 | 6.09 ± 1.20 | 0.67 ± 0.10 |
| Diabetic | 3.98 ± 0.38 | 3.72 ± 0.71^ | 1.51 ± 0.67^ |
| SFZ-treated | 5.25 ± 0.64* | 2.04 ± 0.37* | 2.71 ± 1.34* |

Treatment of diabetic rats with SFZ (200 mg/Kg BW, daily for 9 months) induces changes in the levels of AMP and inosine in total sciatic nerves. Results represent the mean ± SEM of 4 animals.
^ and *significantly different from normal and diabetic, respectively, at P < 0.05.

Analysis of Thermal Nociception, Nerve Conduction Velocity and Degree of Damage to Sensory Fibers in Diabetic Rats We evaluated thermal nociception using the hot-plate withdrawal test, which measures the time between placement of the rat on the hot-plate and the time of withdrawal and licking of the hind paw. This analysis showed that the 5- and 10-week diabetic rats display a significant increase in thermal thresholds (hypoalgesia), as opposed to thermal hyperalgesia (Table 4).

We have also measured motor and sensory digital nerve conduction velocity (MNCV and SNCV, respectively) and evaluated the type and degree of fiber damage in diabetic rats using the neurometer. The results obtained (Table 5) indicate that we can detect significant behavioral (Table 4) or functional (Table 5) differences in the diabetic state, and that these tests can allow the identification of effective therapies based on the partial or complete improvement of their outcomes.

TABLE 4

Effect of diabetes on thermal thresholds.

| Group (n) | 0 time (before induction of experimental diabetes | 5 weeks | 10 weeks |
|---|---|---|---|
| Control (8) | 8.79 ± 0.38 | 8.20 ± 2.54 | 6.82 ± 0.48 |
| Diabetic (7) | 8.47 ± 0.44 | 11.38 ± 3.40* | 10.63 ± 1.19** |

Results shown represent the time, expressed in seconds, until paw is removed from heat source. Results shown represent the means ± SEM.
*P < 0.05; **P < 0.01 (ANOVA followed by comparisons for all pairs using Tukey-Kramer HSD T).

TABLE 5

Effect of diabetes on nerve conduction velocity

|  | MNCV (m/s) | SNCV (m/s) | 2000 Hz (mA) LM | 250 Hz (mA) SM | 5 Hz (mA) SU |
|---|---|---|---|---|---|
| Normal | 58.1 ± 0.4 | 42.5 ± 0.4 | 0.37 ± 0.02 | 0.16 ± 0.01 | 0.16 ± 0.01 |
| Diabetic | 48.2 ± 1.4* | 38.6 ± 0.6* | 0.60 ± 0.05* | 0.25 ± 0.02* | 0.26 ± 0.02* |

Normal and diabetic male Wistar rats (10-15 per group). Diabetes was induced by a single i.p. injection of streptozotocin (50 mg/kg). Measurements were performed at 3 months and comprised; motor NCV (MNCV), sensory digital NCV (SNCV) and quantitative sensory testing of large myelinated (LM), small myelinated (SM) and small unmyelinated (SU) fibers. Results shown represent the mean ± SD.
*significantly different from normal at P < 0.05 as determined by Student's t test.

SUMMARY OF RESULTS

These results indicate that: 1) SFZ prevents the development of tactile allodynia in experimentally diabetic rats through a mechanism at least partially independent of oxidative stress (FIG. 1 and FIG. 2); 2) NFkB-dependent pathways are important for the development of tactile allodynia in experimental diabetes (Table 1); 3) Induction of experimental diabetes leads to increased expression of p65 NFkB in sciatic nerves (FIG. 3, right panel); 4) SFZ treatment prevents the increase in p65 NFkB in diabetic nerves (FIG. 3 right panel); 5) The thermal nociception test and the neurometer analysis are adequate to address the issue of whether the protective effects of SFZ on tactile allodynia extend to other behavioral and functional alterations that characterize the diabetic neuropathy (Tables 4 and 5). 6) Based on the information collected at this stage of the project, the prevention of tactile allodynia by SFZ in diabetic rats is more likely to reflect regulation of NFkB expression/activity than changes in the levels of other putative targets such as adenosine/inosine, NO and PGE2 (Tables 2-3, FIGS. 5-7).

Having described the invention we claim the following:

1. A method of treating abnormal pain perception associated with diabetic neuropathy in a subject, the method comprising: administering to a subject having diabetes a therapeutically effective amount of a pharmaceutical composition comprising the amount of the pharmaceutical composition comprising sulfasalazine the amount of the pharmaceutical composition comprising sulfasalazine being effective to relieve abnormal pain perception associated with diabetic neuropathy, wherein the abnormal pain perception are tactile allodynia and thermal hypoalgesia.

2. The method of claim 1, the amount of the pharmaceutical composition administered to the subject being that amount effective to inhibit NFkB expression in nerves involved in nociception in the diabetic subject.

3. The method of claim 1, the pharmaceutical composition including a pharmaceutically acceptable carrier and/or diluent.

4. The method of claim 1, the pharmaceutical composition being administered by injection, by topical application or by the oral route.

5. A method of treating abnormal pain perception associated with peripheral neuropathy, the peripheral neuropathy associated with an increase in NFkB expression in nerves involved in nociception in a subject, the method comprising:
administering to the subject a therapeutically effective amount of a pharmaceutical composition comprising sulfasalazine the amount of the pharmaceutical composition comprising sulfasalazine being effective to relieve abnormal pain perception associated with peripheral neuropathy wherein the abnormal pain perceptions are tactile allodynia and thermal hypoalgesia.

6. The method of claim 5, the amount of the pharmaceutical composition administered to the subject being that amount effective to inhibit NFkB expression in nerves involved in nociception in the subject.

7. The method of claim 5, the pharmaceutical composition including a pharmaceutically acceptable carrier and/or diluent.

8. The method of claim 5, the pharmaceutical composition being administered by injection, by topical application or by an oral route.

9. A method of inhibiting NFkB expression and increasing p-CREB level in nerves involved in nociception in a subject with a abnormal pain perception associated with peripheral neuropathy, the method comprising:
administering to the subject a therapeutically effective amount of a pharmaceutical composition comprising of sulfasalazine the amount of the pharmaceutical composition comprising sulfasalazine being effective to relieve abnormal pain perception associated with peripheral neuropathy wherein the abnormal pain perceptions are tactile allodynia and thermal hypoalgesia.

10. The method of claim 9, the amount of the pharmaceutical composition administered to the subject being that amount effective to inhibit NFkB expression in nerves involved in nociception in the subject.

11. The method of claim 9, the pharmaceutical composition including a pharmaceutically acceptable carrier and/or diluent.

12. The method of claim 9, the pharmaceutical composition being administered by injection, by topical application, or by an oral route.

* * * * *

UNITED STATES PATENT AND TRADEMARK OFFICE
CERTIFICATE OF CORRECTION

PATENT NO. : 7,964,585 B2
APPLICATION NO. : 11/685377
DATED : June 21, 2011
INVENTOR(S) : Liliana Berti-Mattera et al.

It is certified that error appears in the above-identified patent and that said Letters Patent is hereby corrected as shown below:

Column 15, lines 37-46 replace claim 1:

"1. A method of treating abnormal pain perception associated with diabetic neuropathy in a subject, the method comprising: administering to a subject having diabetes a therapeutically effective amount of a pharmaceutical composition comprising the amount of the pharmaceutical composition comprising sulfasalazine the amount of the pharmaceutical composition comprising sulfasalazine being effective to relieve abnormal pain perception associated with diabetic neuropathy, wherein the abnormal pain perception are tactile allodynia and thermal hypoalgesia."

Change to:

--1. A method of treating abnormal pain perception associated with diabetic neuropathy in a subject, the method comprising: administering to a subject having diabetes a therapeutically effective amount of a pharmaceutical composition comprising sulfasalazine the amount of the pharmaceutical composition comprising sulfasalazine being effective to relieve abnormal pain perception associated with diabetic neuropathy, wherein the abnormal pain perception are tactile allodynia and thermal hypoalgesia.--.

Signed and Sealed this
Seventeenth Day of January, 2012

David J. Kappos
*Director of the United States Patent and Trademark Office*